United States Patent
Kasting, Jr. et al.

(10) Patent No.: US 6,455,017 B1
(45) Date of Patent: Sep. 24, 2002

(54) METHOD AND MOBILE APPARATUS FOR WASHDOWN AND SANITIZING

(76) Inventors: John R. Kasting, Jr., 6614 McCain Blvd., Waxhaw, NC (US) 28173; Dwayne H. Joines, 7511-31 Cove Point Dr., Raleigh, NC (US) 27613; John V. Winings, 1017 Jones Wynd Rd., Wake Forest, NC (US) 27587

( * ) Notice: Subject to any disclaimer, the term of this patent is extended or adjusted under 35 U.S.C. 154(b) by 0 days.

(21) Appl. No.: 09/252,608

(22) Filed: Feb. 4, 1999

(51) Int. Cl.[7] .............................. A61L 2/00; B08B 3/00; A01G 25/09; C02F 9/00
(52) U.S. Cl. ...................... 422/292; 422/300; 422/305; 134/95.3; 239/146; 239/305; 239/311; 239/318; 239/526; 210/241; 210/261; 210/760
(58) Field of Search ............................ 422/3, 28, 29, 422/115, 186.09, 186.12, 186.14, 186.21, 186.08, 291, 292; 134/2, 18, 26, 29, 36, 40, 42, 28, 30, 34, 95.3; 239/146, 303, 304–305, 375, 378, 310, 311, 318, 526, 590, 575, 690; 210/261, 241, 266, 760

(56) References Cited

U.S. PATENT DOCUMENTS

| | | | | |
|---|---|---|---|---|
| 3,687,156 A | * | 8/1972 | Minich, Jr. et al. | 137/334 |
| 3,931,790 A | * | 1/1976 | Franz | 118/73 |
| 4,954,321 A | * | 9/1990 | Jensen | 422/186.19 |
| 5,368,815 A | * | 11/1994 | Kasting, Jr. et al. | 422/3 |
| 5,470,461 A | * | 11/1995 | Ban et al. | 210/188 |
| 5,493,754 A | * | 2/1996 | Gurstein et al. | 15/321 |
| 5,641,456 A | * | 6/1997 | Rosenauer | 422/29 |
| 5,815,869 A | * | 10/1998 | Hopkins | 8/158 |
| 5,839,155 A | * | 11/1998 | Berglund et al. | 15/321 |
| 6,080,313 A | * | 6/2000 | Kelada | 210/631 |

* cited by examiner

Primary Examiner—Robert J. Wardern, Sr.
Assistant Examiner—Monzer R. Chorbaji (57) ABSTRACT

Detergent cleaning is combined with ozone disinfection in a single, preferably mobile sanitizing unit. A detergent cleaning solution, preferably under pressure, is directed onto a surface to be cleaned. Subsequently, an aqueous ozone rinse is applied to the surface following removal of soils by the detergent. Because the ozone rinse functions to sanitize the target and remove residual detergent, and works best when delivered without substantial pressure, construction and ozone generation are simplified.

9 Claims, 6 Drawing Sheets

METHOD AND MOBILE APPARATUS FOR WASHDOWN AND SANITIZING

FIELD OF THE INVENTION

The present invention relates to washing and sanitizing of surfaces such as food-preparation areas, piping, industrial equipment, and storage tanks; and more particularly to systems that utilize ozone as the sanitizing agent.

BACKGROUND OF THE INVENTION

The beneficial properties of ozone have been recognized and applied for many decades. Ozone has been used as a disinfectant to destroy bacteria and certain viruses in drinking water and in air, as a deodorizer for air and sewage gases, as a bleach, and as an oxidizing agent in various chemical processes. Typically, ozone is utilized as a gas or dissolved in water.

The use of ozone as a sterilant has heretofore been confined largely to specialty applications, e.g., flow-through disinfecting of dialysis equipment (see U.S. Pat. No. 5,641,456) and sterilization of medical instruments (see U.S. Pat. No. 5,520,893). More widespread adoption of ozone cleaning equipment has been hampered by the constraints involved in creating and delivering aqueous ozone solutions.

Ozone, or $O_3$, is an unstable molecule that may be formed by subjecting ordinary molecular oxygen to ultraviolet radiation or to forms of electric discharge (such as coronas and sparks). Ozone quickly breaks down, reverting to molecular oxygen or reacting with surrounding species, and so cannot easily be stored; for a system to be practical, ozone must be generated on site at the time of use. Moreover, because of its reactivity, ozone cannot be combined with detergents or other cleaning agents, since the these are vulnerable to ozone attack; in effect, the ozone will destroy both its own effectiveness and that of the cleaning agent rather than attacking pathogens. Consequently, the delicate nature of the ozone molecule and its incompatibility with conventional cleaning agents has limited the applications of ozone cleaning.

DESCRIPTION OF THE INVENTION

Brief Summary of the Invention

In accordance with the present invention, the benefits of detergent cleaning are combined with ozone disinfection in a single, preferably mobile sanitizing unit. The invention provides means for directing a detergent cleaning solution, preferably under pressure, onto a surface to be cleaned. The invention also provides an aqueous ozone rinse, which is applied to the surface following removal of soils by the detergent. Because the ozone rinse functions to sanitize the target and remove residual detergent, and works best when delivered without substantial pressure, construction and ozone generation are simplified.

The invention is usefully employed to sanitize food-preparation areas, piping, industrial equipment, and storage tanks—virtually any exposed surface not harmed by moisture but capable of accumulating soils and harboring harmful pathogens. Ozone decomposes quickly following application, so the ozonated aqueous rinse stream leaves no harmful residues or toxic byproducts. To ensure a high degree of sterilization, the ozone should be present in the rinse stream in an amount ranging from 0.1 ppm to 1.5 ppm, and preferably approximately 0.7 ppm.

The invention also provides a method of cleaning and sanitizing a surface, the method comprising the steps of providing a source of cleaning solution (which is generally detergent-based) and a source of ozonated water, cleaning the surface by selectively directing the cleaning solution onto the surface under pressure, and rinsing the surface by selectively directing a flow of the ozonated water onto the surface.

BRIEF DESCRIPTION OF THE DRAWINGS

The foregoing discussion will be understood more readily from the following detailed description of the invention, when taken in conjunction with the accompanying drawings, in which.

DETAILED DESCRIPTION OF THE PREFERRED EMBODIMENTS

Figure 1:
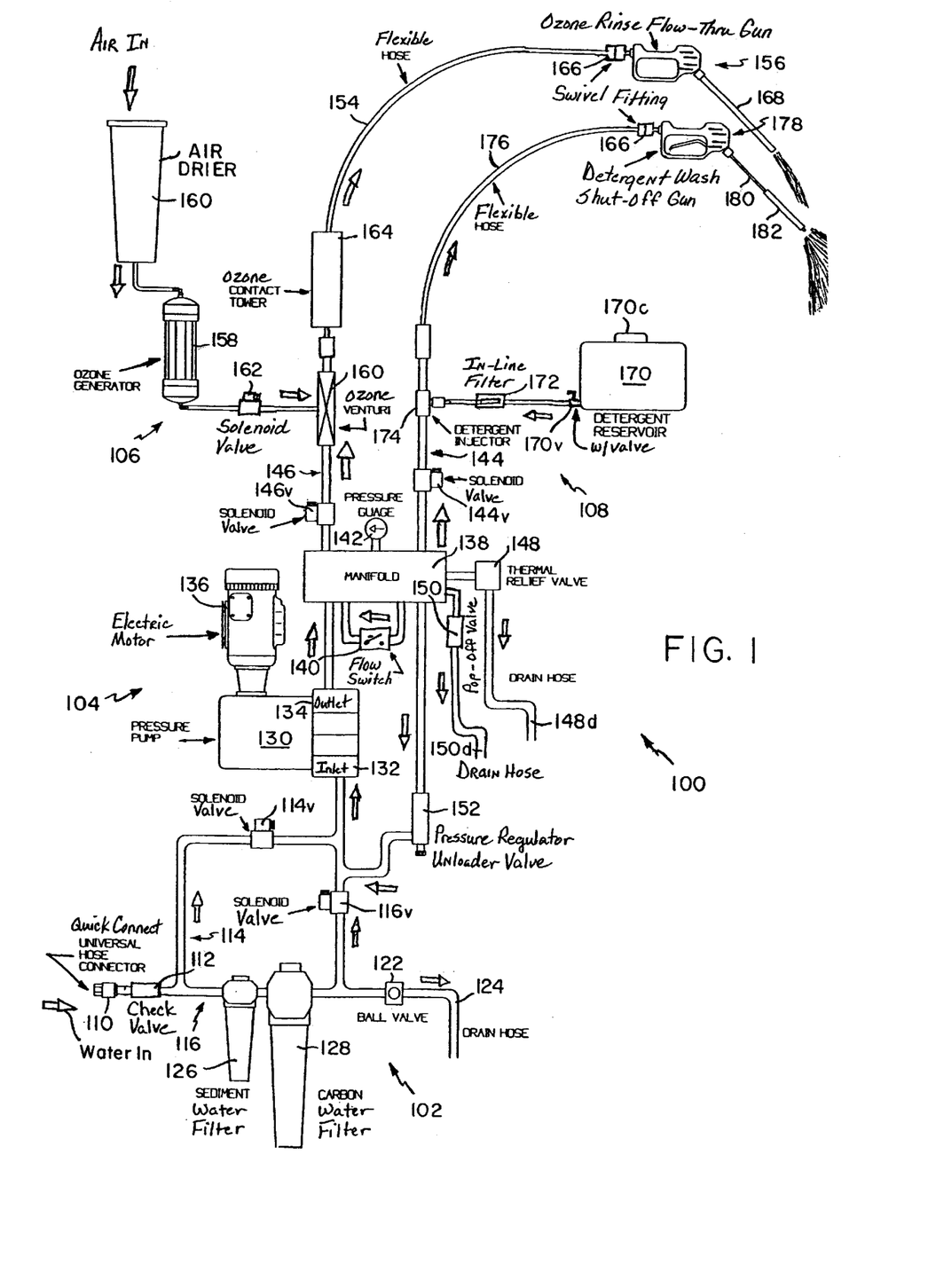
FIG. 1 is a schematic functional diagram of a system in accordance with the present invention.

With reference to FIG. 1, a system 100 embodying the present invention includes a filtration subsystem 102; a pumping subsystem 104; an ozone-generation subsystem 106; and a detergent subsystem 108. Water from a source (such as the municipal water supply) enters the system at an inlet 110, which may be, for example, a universal hose connector. A check valve 112 prevents backflow, and the incoming water can follow either of two flow branches 114, 116, the latter leading through filtration subsystem 102. The direction of flow is selected by a pair of electrically activated solenoid valves 114$v$, 116$v$. A ball valve 122 leads to a system drain 124. The plumbing of branches 114,116 and in the remainder of the system is generally 0.5" diameter piping; plumbing that does not handle ozone may be brass or metal.

Filtration subsystem 102 comprises a sediment filter 126 and a carbon filter 128 to remove from the incoming water undesirable materials, such as chlorine, that would compete with ozone as an oxidizer or otherwise interfere with the action of ozone. Sediment filter 126 may incorporate a replaceable, pleated-polyester sediment filter cartridge sufficient to remove particulates larger than 30 $\mu$m in diameter; a suitable combination is the Ametek 150071 filter housing with a Harmsco model WB30 filter cartridge. Carbon filter 128 likewise contains a replaceable filter element. Ball valve 122 allows water exiting carbon filter 128 to be drained until it runs clear of carbon "fines" following carbon filter cartridge replacement.

Pumping subsystem 104 provides the fluid motive force that directs water through the system. Subsystem 104 includes a pressure pump 130 having an inlet port 132 and an outlet port 134, and an electric motor 136 that powers pump 130. Pump 130 and motor 136 must be sufficient to provide the delivery pressure and flow requirements of the system. Representative values for these parameters may be, for example, 500 psi and 5 gal/min, respectively (typical respective startup values are 300 psi and 4.5 gal/min). The combination of a model P219-EM pump supplied by Giant Corporation with a Leeson 115-volt, 1725 RPM, 1.5 hp motor has been found to provide satisfactory performance.

Water exiting outlet 134 is directed to a manifold 138, which provides a variable connection point among the different plumbing lines and components downstream of pumping subsystem 104. The selected flow through manifold 138 is determined by a flow switch 140. A pressure gauge 142 associated with manifold 138 provides a visual indication of internal system pressure.

From manifold 138, water can be selectably directed through a cleaning line 144 or a rinse line 146; the flows through lines 144, 146 are controlled by a pair of solenoid valves 144$v$, 146$v$, respectively. Regardless of which line is selected, the water flowing through manifold 138 remains in fluid communication with a thermal relief valve 148, a pop-off valve 150, and a pressure-unloading bypass valve 152. Thermal relief valve 148 diverts water to a drain hose 148$d$ if temperatures exceed a predetermined limit. Dumping water to the drain causes the system 100 to demand additional water, and this fresh supply reduces the temperature of the circulating water. Bypass valve 152 controls the pressure through the cleaning line 144, recirculating water through branch 114 and thereby limiting the entry of additional water into the system when the user is not actively discharging water for cleaning. Pop-off valve 150 leads to a drain hose 150$d$, and serves as a back-up safety device to relieve pressure should bypass valve 152 fail. As still another safety feature, it is possible to incorporate a timed shut-off valve that prevents the motor from recycling liquid for more than a pre-set time (e.g., 30 sec to 1 min), thereby preventing the motor from overheating.

Water passing through rinse line 146 is ozonated by ozone-generation subsystem 106, and is thereafter conducted through a flexible hose 154 to exit through a hand-held ejection device 156, described in greater detail below. Ozone-generation subsystem 106 comprises an ozone generator 158, which supplies ozone for injection into rinse line 146 by means of a venturi 160. The ozone is created from air that has been dried in an air drier 160, since moisture can interfere with the production of ozone. Air drier 160 may utilize a silica and alumina dessicant that offers low resistance to air travel. A solenoid valve 162 controls the flow of ozone into venturi 160. Ozone generator 158 may contain a series of corona discharge vacuum tubes housed within separate transparent cylinders, which are themselves disposed within a stainless-steel chamber. For example, each of four corona tubes may be housed within a separate transparent 1"-diameter 316L cylinder mounted and centered within the chamber by a flexible porous spacer. The tubes themselves, charged with inert gases (generally argon and neon) and activated by the output of a high-voltage (e.g., 9000 volt) transformer, are separated from the wall of the chamber by an air gap. The electric field between the tube electrodes and the grounded tube chamber causes ozone (preferably at a level of 0.2 ppm per tube for a total output of 0.8 ppm) to form from oxygen in the air gap.

Ozone is drawn into rinse water by the action of venturi 160. The fluid flow path through venturi 160 gradually narrows, causing water exiting the constriction to flow at a higher rate and creating negative pressure that pulls ozone from generator 158 into the flowing water. The ozone-charged water exiting venturi 160 flows through an ozone contact tower 164, which slows the motive flow rate in order to enhance the solubility of ozone gas. The motive flow pressure into the inlet of venturi 160 may be maintained at 80 psi, with an outlet pressure differential of at least 35–40 psi.

Contact tower 164 is configured as a closed cylinder chamber designed to restrict ozone bubbles to a slow ascent, ensuring their dispersion within the flowing liquid. Preferably, contact tower 164 enforces a 20-sec residence time period during which off-gassing is prevented, allowing for full ozone absorption to ensure maximum concentration in the rinse stream. The selected residence time and the flow rate dictate the dimensions of tower 164, which may be achieved simply by selecting a conforming diameter and height, or through the use of elbows or eccentric fittings. The plumbing in rinse line 146 downstream of venturi 160 is stainless steel or ozone-resistant plastic (e.g., schedule 80 PVC).

Ejection device 156 may be a flow-through gun connected to hose 154 by means of a swivel fitting 166, and terminating in a wand or lance 168. Device 156 does not permit the user to interrupt the flow of water through wand 168, since backpressure on venturi 160 would interfere with its operation and reduce or defeat the introduction of ozone into the rinse stream.

Fluid flow through cleaning line 144 occurs under pressure, generally 80–100 psi. A detergent reservoir 170, equipped with an outlet valve 170$v$ and covered by a removable cap 170$c$, may contain a commercial liquid detergent (preferably a biodegradable, low-foaming detergent). An in-line filter 172 removes contaminants and agglomerations from the detergent, which is introduced into washing line 144 by means of an injector 174. Injector 174 is configured to combine detergent with flowing water in a predetermined proportion, e.g., in the range of 0.251–3.0 oz/gal.

Detergent-containing wash water travels through a flexible hose 176 to a shut-off gun 178 that terminates in a wand 180. Unlike flow-through gun 156, the hand-held portion of gun 178 contains a trigger that allows the user to regulate the flow of pressurized liquid through wand 180 (which may terminate in an adjustable spray head or nozzle 182 that provides a variable spray plume). The exit pressure may, for example, be varied from 10 to 100 lbs/in$^2$.

In operation, the user selects "wash" or "rinse" operation using selector switch 140. In the wash mode, water need not pass through filter subsystem 102; accordingly, selection of this mode results in the direction of incoming water along path 114 through closure of solenoid valves 116$v$, 146$v$ and opening of valves 114$v$, 144$v$. Pumping subsystem 104 is activated, and water flows through manifold 138 into line 144, picking up detergent and exiting the system from nozzle 182 when the user activates gun 178. During the washing operation, the user controls the exit pressure and directs the detergent-containing water at the surfaces to be cleaned. The combination of detergent and high pressure dislodges visible and water-soluble soils, and bathes the surface in a solution that emulsifies oily soils. Desirably, the outlet pressure provides satisfactory cleaning action with a minimum of overspray and bounce-back.

Residual detergent and emulsified soil are removed from the surfaces by the rinse stream, which the user activates by changing the setting of selector switch 140. This action causes closure of solenoid valves 114$v$, 144$v$ and opening of valves 116$v$, 146$v$, which, in turn, causes water to be diverted through filtration subsystem 102 and subsequently into venturi 160 via line 146. In addition, ozone generator 158 is activated and solenoid 162 opened to permit ozone to be drawn into the flow through venturi 160. Because gun 156 does not impede flow, the exit of ozonated water through wand 168 is substantially continuous and without substantial pressure. In particular, the flow is desirably around 5 gal/min for most commercial applications, with pressure essentially equal to the exit pressure from venturi 160.

The user directs the low-pressure flow of ozonated water over the previously washed surfaces to rinse off the residual detergent and remaining soils, and to kill microbial and viral pathogens. It should be stressed that the rinsing operation is not intended to dislodge soils, so high flow pressures, which are not sustainable from a system perspective, are not necessary from an operating perspective.

The invention is well-suited to a wide variety of operating environments and is effective on most surfaces, including smooth (e.g., stainless steel) and porous (e.g., concrete) surfaces. Operation can occur in ambient air temperatures ranging from 20 to 80° F.

Figure 2:
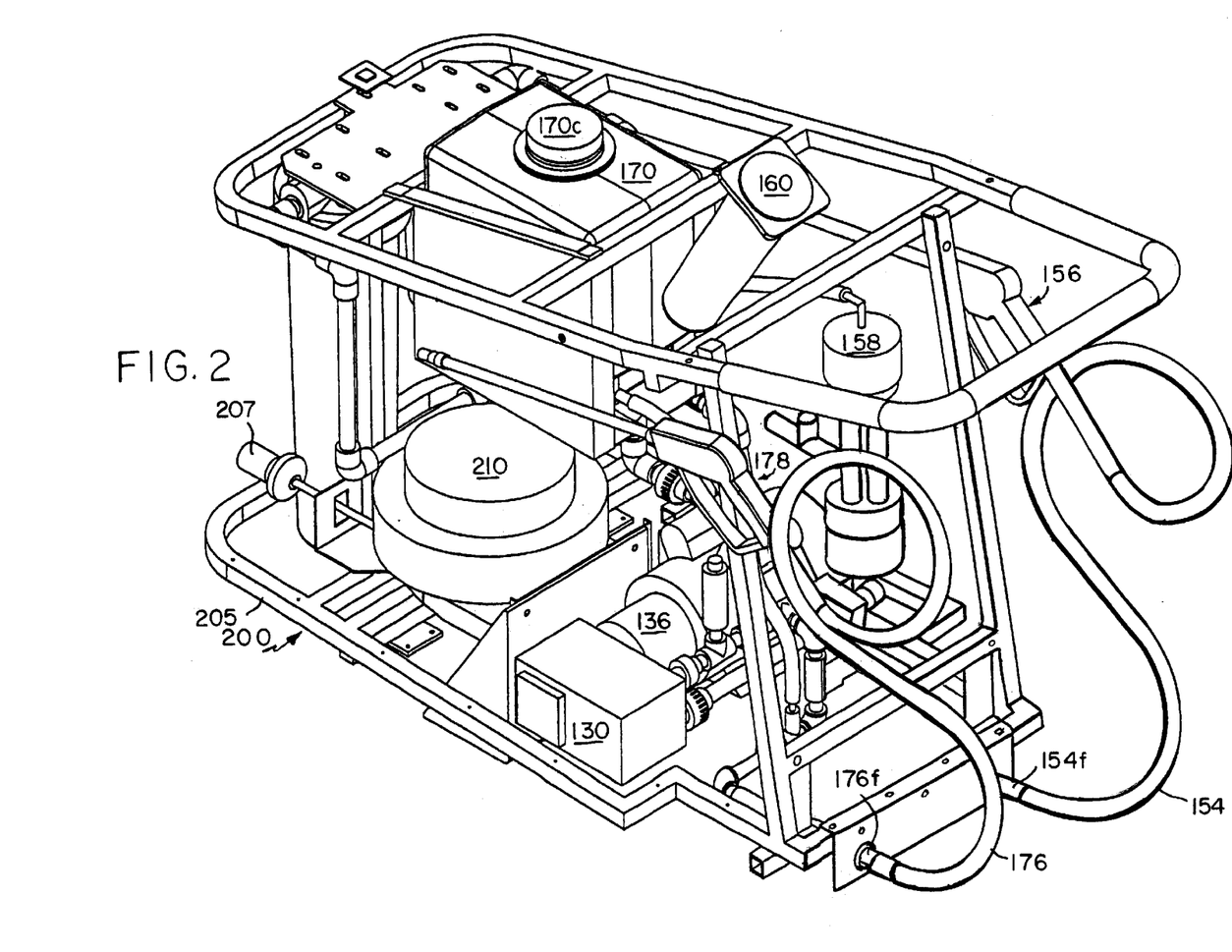
FIG. 2 is an isometric view, taken from the front, of an embodiment of the invention with the housing removed to reveal internal system components, with some components removed for clarity.
Figure 3:
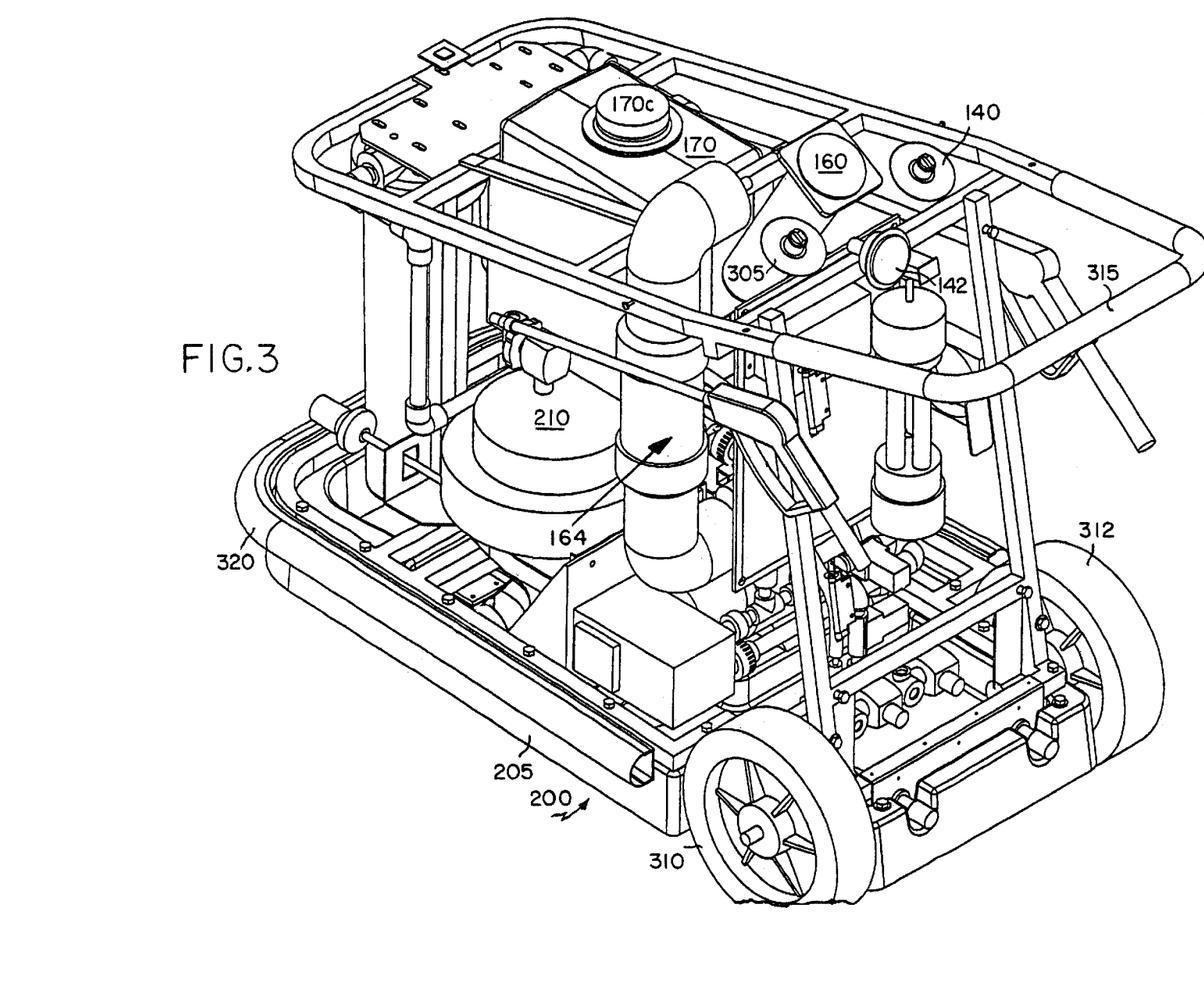
FIG. 3 is another view of the embodiment shown in FIG. 2, with additional internal components rendered.

FIGS. 2 and 3 illustrate the internal components of a working embodiment of the invention. With reference to FIG. 2, mechanical components such as pump 130 and motor 136 are mounted on a chassis 200, which includes a steel machine frame 205. Power is supplied by an electrical cord and outlet plug 207, which may be configured for 120-volt or 240-volt compatibility depending on system design. A long (e.g., 45-foot) electrical cord is retractably housed in a compartment 210. Hoses 154, 176 extend from respective plumbing connectors or fittings 154$f$, 176$f$ to respective rinse and wash guns 156, 178, which are housed as set forth below. To afford freedom of operation and reach into confined areas, hoses 154, 176 may be 25–40 feet in length.

FIG. 3 shows additional interior components of the illustrated embodiment, with hoses 154, 176 omitted for clarity. Flow-control switch 140 is disposed near pressure gauge 142 and a main power switch 305; these components are mounted on a single panel, as shown in subsequent figures, for convenient access and visibility. A pair of wheels 310, 312 are rotatably mounted on chassis 200, as is a pivotally mounted wheel (not shown) at the opposite end of frame 205, allowing the unit to be conveniently rolled and steered. The user pushes or pulls the unit by means of a handle 315. An elastomeric (e.g., rubber) bumper 320 protects both the unit and obstacles it might strike during use or transport.

Figure 4:
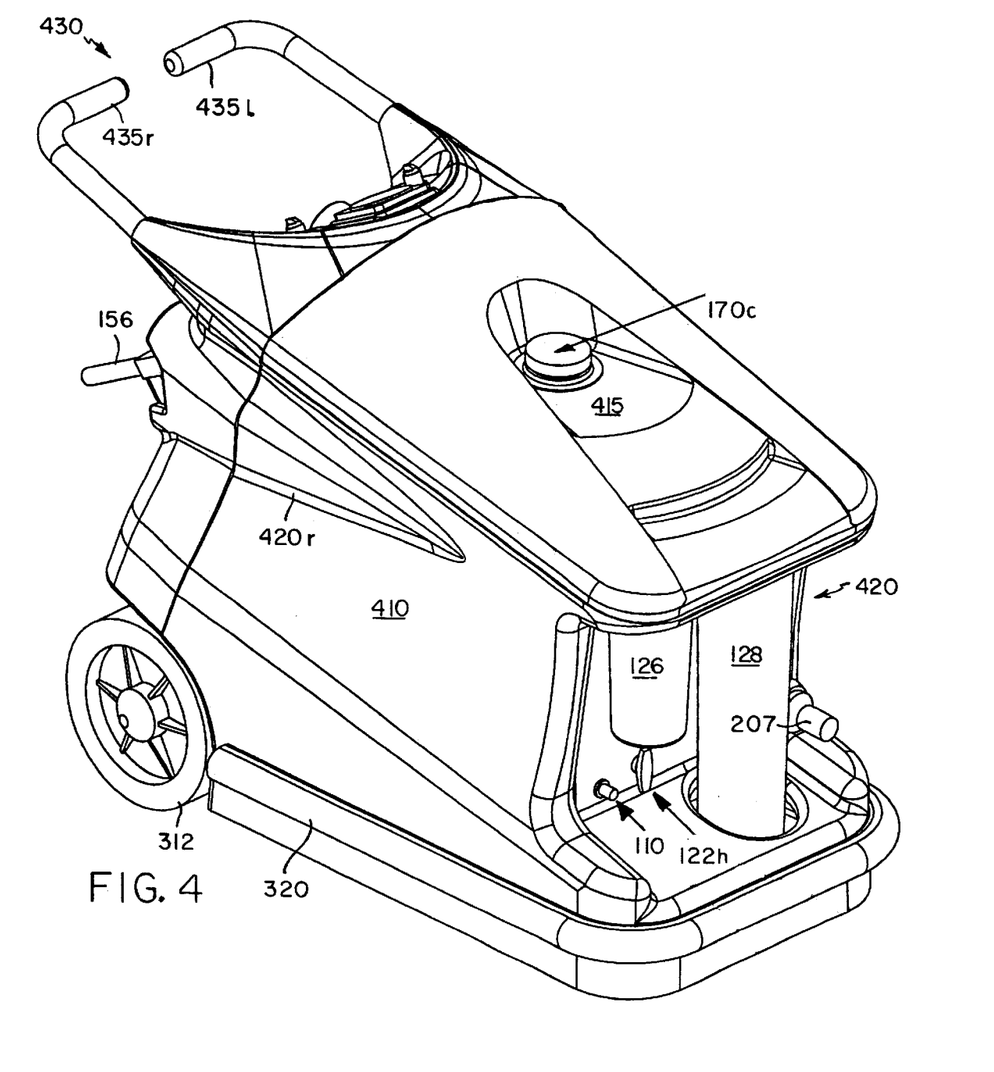
FIG. 4 is an isometric view, taken from the rear, of another embodiment of the invention with the exterior housing in place.
Figure 5:
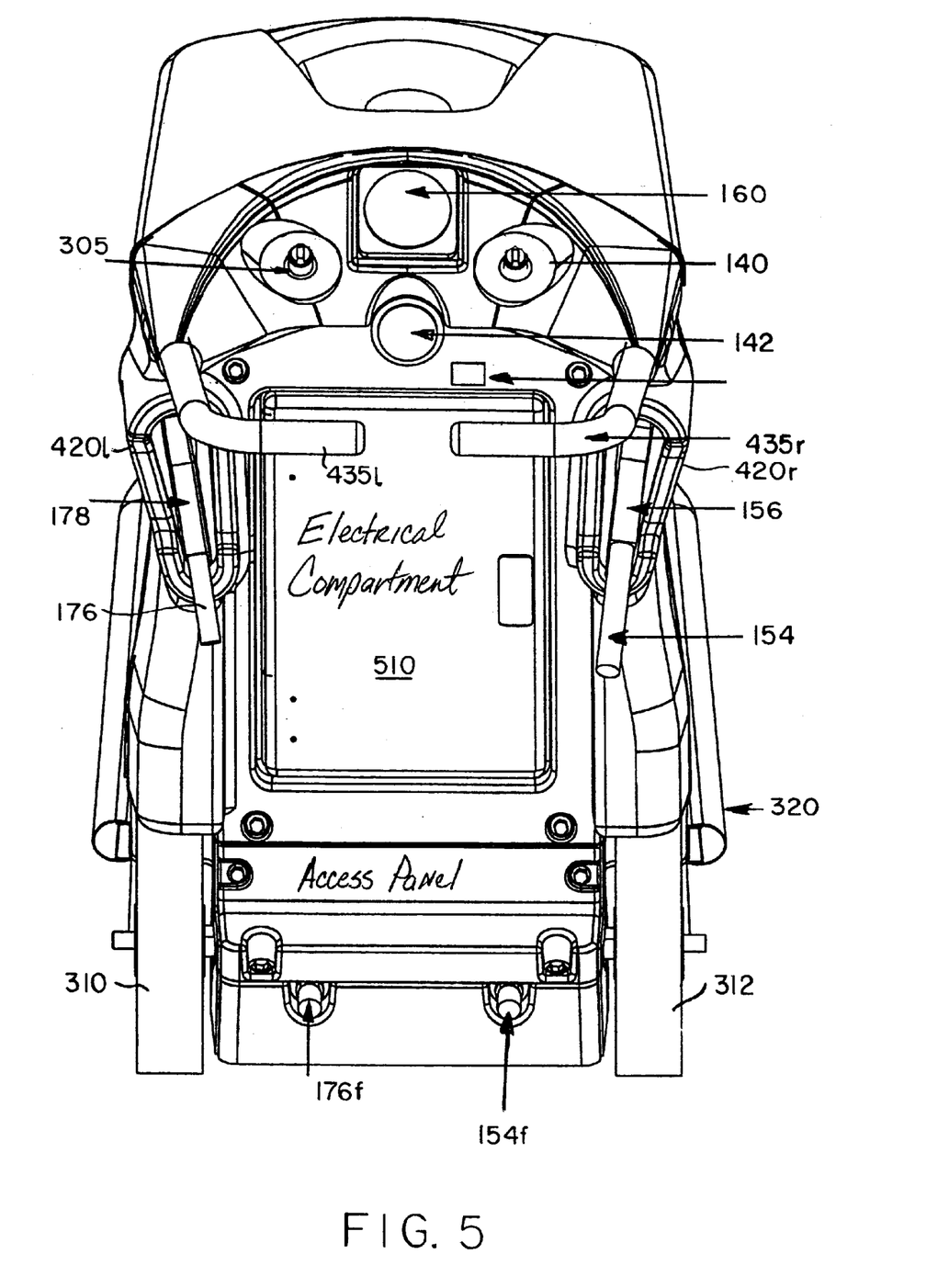
FIG. 5 is a front elevational view of the embodiment depicted in FIG. 4.
Figure 6:
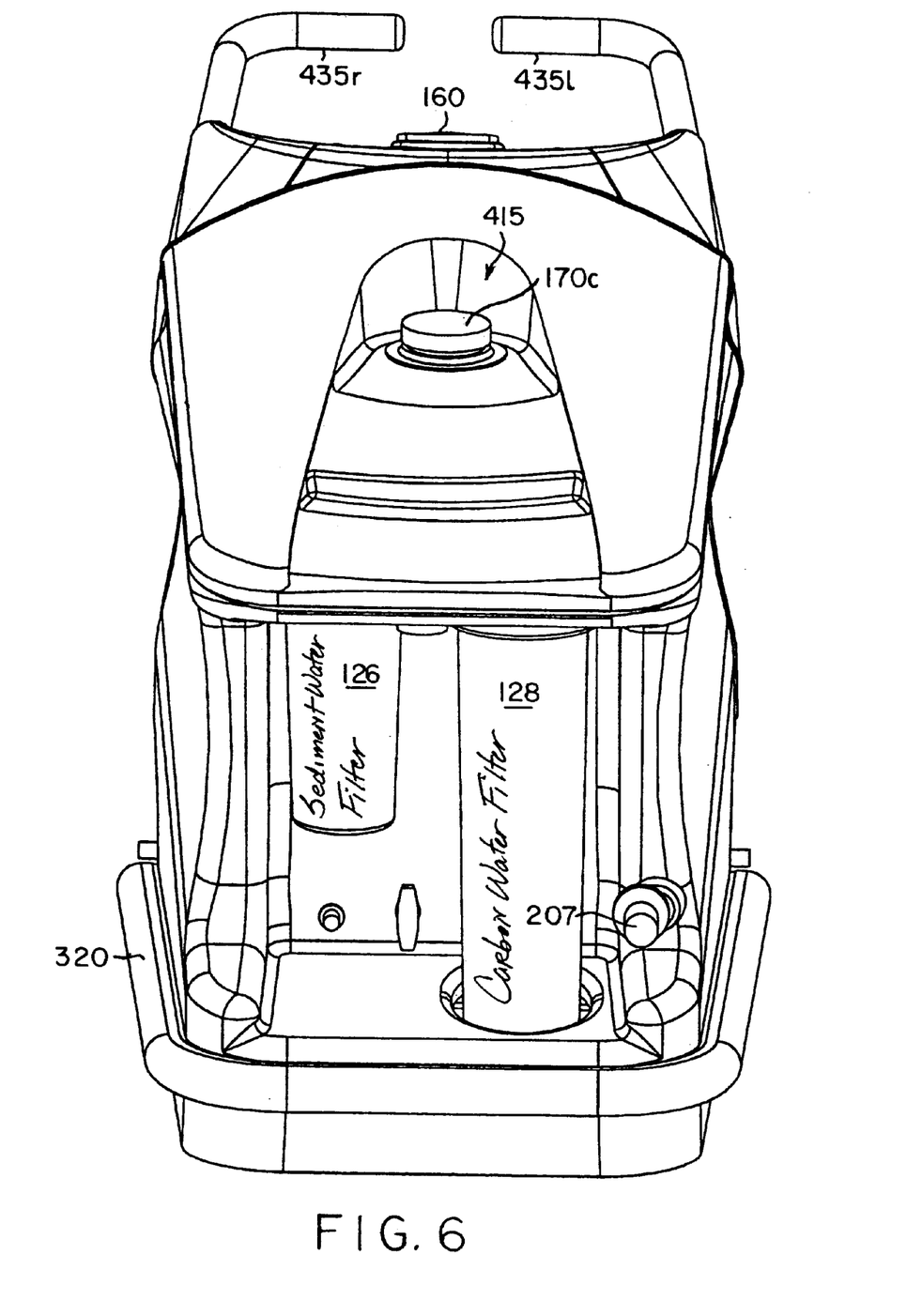
FIG. 6 is a rear elevational view of the embodiment depicted in FIG. 4.

FIGS. 4–6 illustrate the components invention surrounded by a protective housing 410, which is fabricated from a corrosion- and ozone-resistant material, preferably heavy-duty plastic. The housing has a cut-away portion 415 that affords access to detergent reservoir 170 via cap 170$c$, and a recessed portion 420 that exposes filters 126, 128, inlet 110 (which the user connects to the water supply) and the handle 122$h$ used to operate ball valve 122. A pair of compartments 420$_r$, 420$_l$ raised from the surface of housing 410 hold rinse and wash guns 156, 178, respectively. The embodiment depicted FIGS. 4–6 is provided with a different style of handle 430, which comprises a pair of bars fitted with molded, elastomeric grips 435$_r$, 435$_l$. The space between the bars allows for convenient storage of the hoses over the grips. With particular reference to FIG. 5, an electrical compartment 510 houses suitable control circuitry, conventional in the art, for operating the solenoid valves and ozone subsystem 106 in response to the position of flow switch 140.

It should be emphasized that the illustrated embodiments are exemplary only, and numerous design variations are possible. For example, guns 156, 178 can be combined into a single hand-held unit, which may also include switch 140. In this design, the single gun is equipped with a trigger, but switch 140 is mechanically configured to disable the trigger (and enforce an open-flow condition) when the "rinse" mode is selected. Lines 144, 146 merge into a single hose downstream of injector 174 and contact tower 164, and the hose is connected to the gun along with an electrical cable running from the control circuitry.

It will therefore be seen that the foregoing represents a highly convenient and effective approach to cleaning and disinfection of a wide variety of industrial, commercial, and even household surfaces. The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed.

What is claimed is:

1. A mobile cleaning and sanitizing system comprising
   a controllable fluid manifold having an inlet and at least first and second outlets, said manifold being switchable between a first condition which connects the inlet to the first outlet and a second condition which connects the inlet to the second outlet;
   a water source providing water at a selected pressure to said inlet;
   a hand-held washing device;
   a first fluid path extending between the first manifold outlet and the hand-held washing device, said first path including a controllable first valve;
   a hand-held rinsing device;
   a second fluid path extending between the second manifold outlet and the hand-held rinsing device, said second path including, in series, ozone injection means and a controllable second valve;
   a controllable ozone generator in fluid communication with the ozone injection means and which, when activated, provides ozone to the ozone injection means for mixing with any water flowing therethrough, and
   switch means connected to and for controlling said manifold, said valves and said ozone generator, said switch means being switchable between
   a first state which switches the manifold to said first state, opens and said first valve and closes said second valve, and
   a second state which switches the manifold to said second condition, closes the first valve, opens the second valve while activating the ozone generator
   so that ozone is provided to the ozone injection means only when water is actually flowing from the water source along the second path to the rinsing device.

2. The system defined in claim 1 and further including
   a source of cleaning solution, and
   means connecting the cleaning solution source to the first fluid path for mixing with the water flowing therethrough when the switch means is in said first state.

3. The system defined in claim 2 wherein the washing device includes a hand-operated valve for controlling water flow from said washing device.

4. The system defined in claim 1 wherein the water source comprises
   a continuous water supply;
   a pump having a pump connected to the manifold inlet, and a pump inlet, and
   means connecting the water supply to the pump inlet.

5. The system defined in claim 4 wherein the connecting means include
   a first fluid conduit connected between the water supply and the pump inlet, said first conduit including controllable first valve means connected to and controlled by the switch means and which open only when the switch means is in said first state,
   a second fluid conduit connected between the water supply and the pump inlet in parallel with the first fluid path, said second conduit including, in series, filter means and controllable second valve means connected to and controlled by the switch means and which open only when the switch means is in said second state
   so that only unfiltered water flows along the first path to the washing device and only filtered water flows along the second to the rinsing device.

6. The system defined in claim 1 wherein the ozone injection means comprise a venturi device which draws ozone from the ozone producing means into the water flowing from the water source along the second path to the rinsing device.

7. The system defined in claim 6 wherein the ozone injection means also include a control tower connected in the second path down-stream from the venturi device to maintain ozone-water contact for a pre-determined residence time in the second path.

8. The system defined in claim 7 wherein the ozone producing means comprise a plurality of corona discharge tubes.

9. The system defined in claim 7 wherein the ozone producing means, the venturi and the contact tower cooperate to create in the water flowing to the rinsing device an ozone concentration ranging from 0.1 ppm to 1.5 ppm.

* * * * *